US005643608A

United States Patent [19]

McKinzie et al.

[11] Patent Number: 5,643,608
[45] Date of Patent: Jul. 1, 1997

[54] LOW PH GERMICIDAL IODINE COMPOSITIONS HAVING ENHANCED STABILITY

[75] Inventors: Michael D. McKinzie; Murray W. Winicov, both of Kansas City, Mo.

[73] Assignee: West Agro, Inc., Kansas City, Mo.

[21] Appl. No.: 609,515

[22] Filed: Mar. 1, 1996

[51] Int. Cl.$^6$ .................................................. A61K 33/18
[52] U.S. Cl. ........................... 424/667; 424/668; 424/669
[58] Field of Search ............................... 424/667, 668, 424/669, 80

[56] References Cited

U.S. PATENT DOCUMENTS

| | | | |
|---|---|---|---|
| 1,676,554 | 7/1928 | Hoopman. | |
| 1,896,171 | 2/1933 | Harry. | |
| 3,028,299 | 4/1962 | Winicov et al. | 167/17 |
| 3,914,411 | 10/1975 | Askienazy et al. | 424/150 |
| 4,271,149 | 6/1981 | Winicov | 424/150 |
| 4,297,232 | 10/1981 | Ruben | 252/187 R |
| 4,320,114 | 3/1982 | Denzinger et al. | 424/80 |
| 4,575,491 | 3/1986 | Pollack et al. | 436/125 |
| 4,839,080 | 6/1989 | Jungermann et al. | 252/107 |
| 4,849,215 | 7/1989 | Gottardi | 424/80 |
| 4,946,673 | 8/1990 | Pollack et al. | 424/80 |
| 4,954,351 | 9/1990 | Sackler et al. | 424/667 |
| 4,985,234 | 1/1991 | Nakamura et al. | 424/45 |
| 5,368,868 | 11/1994 | Winicov | 424/667 |

FOREIGN PATENT DOCUMENTS

| | | |
|---|---|---|
| 448288A1 | 9/1991 | European Pat. Off.. |
| 3313655 | 3/1995 | Germany. |

OTHER PUBLICATIONS

J. American Pharm. Assoc.; vol. 41, 1952, p. 634.
J. Applied Bacteriol., vol. 48, 1980, p. 449–455.
Remingston's Practice of Pharmacy, Martin et al.; Mack Publishing Co., 12th Ed. (1961) 1800.
British Pharmaceutical Codex (1923) 1130.
Winicov et al.; Proc. Int. Symposium of Providone (University of Kentucky, College of Pharm.) (1983), pp. 186–192.

*Primary Examiner*—Phyllis G. Spivak
*Attorney, Agent, or Firm*—Hovey, Williams, Timmons & Collins

[57] ABSTRACT

Stable aqueous iodine/iodide/iodate germicidal compositions are provided which have relatively high quantities of free iodine therein and also substantially maintain the starting amounts of available and free iodine throughout a storage period of at least about three months. The compositions of the invention contain from about 0.01–1.4% by weight available iodine, from about 10–125 ppm free iodine, from about 0.005–0.5% by weight iodate ion, from about 0.1–15% by weight of iodine complexing agent, from about 0.004–0.5% by weight iodide ion, and have a pH of from about 2.0–4.5.

35 Claims, No Drawings

LOW PH GERMICIDAL IODINE COMPOSITIONS HAVING ENHANCED STABILITY

Background of the Invention

1. Field of the Invention

The present invention is broadly concerned with aqueous germicidal iodine/iodide/iodate compositions of very low pH (from about 2–5.5) having enhanced available iodine and free iodine stabilities over extended storage periods of at least about three months. More particularly, the invention pertains to such compositions which contain from about 0.01–1.4% by weight available iodine, from about 10–125 ppm free iodine, from about 0.004–0.50% by weight iodide ion, and from about 0.005–0.5% by weight iodate ion, in combination with an iodine complexing agent. Optional ingredients may include emollients, buffering agents and thickeners.

2. Description of the Prior Art

U.S. Pat. No. 4,271,149 describes aqueous detergent-iodine compositions of the iodine/iodide/iodate variety having pH values of 5–7 with elemental iodine amounts up to about 1% by weight. Typically, representative compositions described within the '149 patent will have free (i.e., uncomplexed) iodine levels of less than 10 ppm. In compositions of this type, two primary competing reactions take place during storage to maintain stability. First, there is some conversion of elemental iodine in the presence of organic matter to iodide ion; second, there is a competing reaction between iodate ion, iodide ion and $H^+$ to form $I_2$. Ideally, these two reactions are balanced so that the $I_2$ content tent of the compositions remains essentially constant.

In recent years, users of germicidal iodine compositions have requested greater and greater amounts of free iodine, e.g., about 20 ppm and above. In order to meet this demand, it is necessary to lower the pH levels of the compositions to achieve these higher free iodine concentrations. However, it was known that at low pH values below 5, the reaction between iodide and iodate to form elemental iodine becomes predominant and can generate excessive amounts of iodine. Hence, products of the type described in the '149 patent, at low pH, would lack requisite long-term stability. Workers in the art have thus faced a heretofore insoluble dilemma: by lowering the pH to achieve and maintain desired higher free iodine levels, the stability of the compositions is very significantly affected, particularly over long storage times.

There is accordingly a real and unsatisfied need in the art for improved aqueous germicidal use compositions of the iodine/iodide/iodate variety which are of very low pH in order to generate/maintain high free iodine levels therein and which are stable over long periods of storage.

SUMMARY OF THE INVENTION

The present invention overcomes the problems outlined above and provides low pH, stable aqueous detergent-iodine germicidal use compositions having a pH of from about 2–5.5 and a free iodine content on the order of 10–125 ppm while retaining acceptable ranges of available iodine and free iodine contents over a room temperature storage period of at least about three months, and more preferably at least about one year. Preferably, substantial maintenance of the amounts of available and free iodine refers to the ability of the compositions to maintain the nominal, as-manufactured amounts of free and available iodine within about ±20%.

Broadly speaking, the compositions of the invention both as originally formulated and after an equilibration period of about one week, include from about 0.01–1.4% by weight available iodine. In the case of hard surface sanitizers, the as-manufactured available iodine content is preferably from about 0.01–0.20% by weight, whereas for topical skin applications, the available iodine has a range of from about 0.10–1.4% by weight. The free iodine content should be from about 10–125 ppm and more preferably from about 25–125 ppm. The iodate ion content of the compositions should be at a level of from about 0.005–0.5% by weight and more preferably from about 0.01–0.4% by weight. The iodide ion content should be from about 0.004–0.50% by weight, and more preferably from about 0.01–0.45% by weight. The pH levels of the compositions should be from about 2–5.5 and more preferably from about 2–4.5.

A prime advantage of the compositions of the invention is the maintenance of extremely high levels of free iodine over extended storage periods. As indicated above, the free iodine content should broadly be from about 10–125 ppm. In more preferred forms, the compositions of the invention maintain a free iodine level of at least about 25 ppm over a storage period at ambient temperature of at least about 3 months, and most preferably at least about 40 ppm. Thus, in the case of hard surface sanitizers, it is desired that they exhibit a free iodine content of at least about 40 ppm over at least a 3 month ambient temperature storage period. For some preparations adapted for topical application to skin, it may be desirable to maintain the free iodine content at a level of from about 20–50 ppm over an ambient temperature storage period of at least 3 months.

The compositions hereof also include a complexing agent which is used in sufficient quantity to insure that the available iodine content of the compositions remains in solution. Generally, the complexing agent should be used at a level of from about 0.1–15% by weight, and more preferably from about 0.2–10% by weight. A variety of complexing agents can be employed, such as those selected from the group consisting of the alkylphenol ethoxylates, alcohol ethoxylates, alcohol alkoxylates, polyalkylene glycol ethers, polyoxyethylene sorbitan monolaurate and monopalmitate, polyvinylpyrrolidone, polyethoxylated polyoxypropylenes, and mixtures thereof.

Normally, compositions in accordance with the invention would include a buffering agent such as an acid selected from the group consisting of citric, acetic, propionic, lactic, phosphoric, salts of the foregoing, and mixtures thereof. Such a buffering agent would normally be used at a level of from about 0.02–1% by weight in order to maintain the desired pH level during extended storage. For ease of use, a thickening agent may also be incorporated into the compositions of the invention. Suitable thickening agents may be selected from the group consisting of the alginates, xanthan gums, cellulose-bearing agents and mixtures thereof, and would ordinarily be used at a level of from about 0.05–1.5% by weight. Emollients are also commonly used in compositions of the invention, such as those selected from the group consisting of glycerine, lanolin and its derivatives, sorbitol, fatty acid esters of polyhydroxylated compounds, propylene glycol, and mixtures thereof. The emollient content would typically be in the range of from about 1–15% by weight.

There are several ways in which the compositions of the invention can be prepared. Generally speaking, in view of the low levels of iodide employed, it may not be convenient to start with a liquid concentrate having the desired iodide:iodine ratio. However, it is possible to start with iodide alone, and to form the desired portion of iodine in situ through oxidation. Alternately, one may employ a concentrated iodine solution (e.g., 57% by weight iodine and 20% by weight iodide ion) at a level which supplies all the desired iodide, followed by adding the remaining iodine through incorporation of crystalline iodine, with stirring. Another alternative is to start with a concentrated iodine solution which provides the desired total iodine (iodine plus iodide) content, but with a higher iodide:iodine ratio than ultimately desired, and then setting the initial pH at a predetermined lower level, in order to induce a fairly rapid conversion of the iodide to iodine through reaction with added extra iodate. This would generally occur within the first day or two after the initial makeup of the compositions, and would be deemed a part of the manufacturing process.

The compositions of the invention may also be prepared directly from mixtures of solid components, e.g., Povidone-iodine powder, an appropriate iodate salt such as sodium iodate crystals, citric acid, and an alkaline salt. These ingredients would be dissolved in water to form the desired composition.

DETAILED DESCRIPTION OF THE PREFERRED EMBODIMENT

The present invention is predicated on the discovery that detergent iodine/iodide/iodate germicidal compositions can be prepared having very low pH values on the order of 2–5.5 in order to generate relatively large amounts of free iodine, while at the same time exhibiting long term stability in terms of the amounts of available and free iodine therein. This is accomplished by a careful selection of the amounts and types of ingredients present in the compositions, such that the competing reactions taking place in the compositions effectively cancel each other out so as to maintain overall compositional stability. The principal equilibrium reactions occurring during storage of the compositions after manufacture are:

I. Organic Material+$I_2 \rightarrow 2I^-$+oxidized organic material

II. $IO_3^- + 5I^- + 6H^+ \rightarrow 3I_2 + 3H_2O$

III. $I_2$+complexor+$I^- \rightarrow$ complexed $I_2 \cdot I^-$

As explained, the goals of the invention are a relatively high free iodine content together with long term stability. Low initial system pH is important to generate the necessary free iodine, because the excess $H^+$ ion drives reaction II to the right. As $H^+$ ion is consumed and the pH rises, reaction II slows down, but this is counterbalanced by the fact that reaction I is also fastest at the outset and itself slows down over time. Thus, reactions I and II are generally balanced throughout the shelf life of the product. Reaction III is also controlled and the formation of excess complexed $I_2$ is avoided because of the consumption of $I^-$ in reactions I and II, thus driving reaction III to the left. In sum therefore, the ongoing competing reactions I–III within the compositions of the invention are effectively balanced over the shelf lives of the products to achieve compositional stability.

The following example sets forth preferred compositions in accordance with the invention as well as stability test results. It is to be understood that this example is presented by way of illustration only and nothing therein should be deemed a limitation upon the overall scope of the invention.

EXAMPLE

The following compositions in accordance with the invention were prepared using three different methods detailed below. The following tables set forth the ingredients used in each formulation (wherein all ingredient data is set forth in terms of percent by weight, and the free $I_2$ data is given as ppm) as well as the three or four month stability data for compositions containing on a nominal weight basis 1.0% available iodine (Table 1), 0.75% available iodine (Table 2), 0.50% available iodine (Table 3), 0.25% available iodine (Table 4), 0.10% available iodine (Table 5), 0.05% available iodine (Table 6), and 0.025% available iodine (Table 7). The available iodine content will typically vary ±10% over the shelf life of the products. The iodate content will decrease during storage and can generally be expected to be completely gone within 2–4 years of room temperature storage. The pH values for the compositions will generally increase, sometimes by as much as 0.5–1 pH unit following initial preparation.

Compositions 1 and 2 of Table 1, and all compositions of Tables 3–7, were manufactured by dissolving all ingredients except for the sodium iodate in aqueous solution, adjusting to the initial pH using a solution of sodium hydroxide, and adding the sodium iodate.

Compositions 3–6 of Table 1 were manufactured by first dissolving all ingredients except the 0.5% sodium iodate in aqueous solution. To this was added 0.06% by weight sodium iodate and the mixture was allowed to react for a period of 2 hours. The pH of the sample was then adjusted to the predetermined initial value using a solution of sodium hydroxide and the 0.5% by weight sodium iodate was then added and dissolved with stirring.

Compositions 7–10 of Table 1 were manufactured in the same manner as compositions 3–6, except using 0.05% by weight sodium iodate prior to the pH adjustment of the sample. After such adjustment, the remainder of the iodate was added.

The compositions of Table 2 were manufactured by dissolving all ingredients in aqueous solution except for the sodium iodate, using an amount of iodine complex providing a predetermined amount of iodide ion. In order to achieve the desired iodide:iodine ratio, crystalline iodine was then added to the solutions with stirring until dissolved. The pH of the sample was then adjusted to the predetermined initial value and the sodium iodate was added, with stirring, until dissolved.

TABLE 1

| | 1% Available Iodine (Nominal) | | | | | | | | | |
|---|---|---|---|---|---|---|---|---|---|---|
| | 1 | 2 | 3 | 4 | 5 | 6 | 7 | 8 | 9 | 10 |
| Povidone K-30 | 0.5 | 2.0 | 10.0 | 10.0 | 10.0 | 10.0 | 10.0 | 10.0 | 10.0 | 10.0 |
| Propylene Glycol | — | 4.0 | — | — | — | — | — | — | — | — |
| Poloxamer 335 | 2.0 | 2.0 | — | — | — | — | — | — | — | — |
| Polyethylene Glycol 400 | 2.0 | — | — | — | — | — | — | — | — | — |
| Aerosol OT-7S | 0.05 | 0.1 | — | — | — | — | — | — | — | — |
| Keltrol | 0.1 | 0.2 | — | — | — | — | — | — | — | — |

TABLE 1-continued

| | 1% Available Iodine (Nominal) | | | | | | | | | |
|---|---|---|---|---|---|---|---|---|---|---|
| | 1 | 2 | 3 | 4 | 5 | 6 | 7 | 8 | 9 | 10 |
| Iodine Complex A[1] | 3.3 | 3.3 | 2.7 | 2.7 | 2.7 | 2.7 | 2.83 | 2.83 | 2.83 | 2.83 |
| Iodide | — | — | .15–.25 | .15–.25 | .15–.25 | .15–.25 | .15–.25 | .15–.25 | .15–.25 | .15–.25 |
| Citric Acid | 0.3 | 0.3 | 0.3 | 0.3 | 0.3 | 0.3 | 0.3 | 0.3 | 0.3 | 0.3 |
| Glycerin | 10.0 | 6.0 | 10.0 | 10.0 | 10.0 | 10.0 | 10.0 | 10.0 | 10.0 | 10.0 |
| Sodium Iodate | 0.5 | 0.5 | 0.5 | 0.5 | 0.5 | 0.5 | 0.5 | 0.5 | 0.5 | 0.5 |
| Water | q.s. 100% | q.s. 100% | q.s. 100% | q.s. 100% | q.s. 100% | q.s. 100% | q.s. 100% | q.s. 100% | q.s. 100% | q.s. 100% |
| Initial pH (Mfg.) | 4.0 | 4.0 | 2.75 | 3.0 | 3.5 | 4.0 | 2.75 | 3.0 | 3.5 | 4.0 |
| Initial pH (4 days) | 4.4 | 4.4 | 3.03 | 3.25 | 3.67 | 3.42 | 3.67 | 4.01 | 4.36 | |
| 2 Mos. pH | 4.6 | 4.6 | 3.47 | 3.67 | 4.10 | 4.42 | 3.66 | 3.89 | 4.02 | 4.56 |
| 4 Mos. pH | 4.8 | 4.8 | 3.56 | 3.71 | 4.12 | 4.43 | 3.71 | 3.90 | 4.20 | 4.50 |
| Initial Available $I_2$ | 1.00 | 1.00 | .94 | .93 | .91 | .88 | .94 | .95 | .93 | .91 |
| 2 Mos. Available $I_2$ | 1.02 | 1.01 | .97 | .97 | .95 | .93 | .96 | .99 | 1.00 | .97 |
| 4 Mos. Available $I_2$ | 1.05 | 1.00 | 1.08 | 1.05 | .99 | .97 | 1.04 | 1.05 | 1.03 | 1.02 |
| Initial Free $I_2$ (ppm) | 10 | 8 | 51 | 56 | 37 | 22 | 56 | 41 | 27 | 12 |
| 2 Mos. Free $I_2$ (ppm) | 17 | 12 | 77 | 60 | 39 | 24 | 67 | 48 | 31 | 10 |
| 4 Mos. Free $I_2$ (ppm) | 18 | 16 | 67 | 52 | 35 | 22 | 53 | 42 | 27 | 20 |

[1]The iodine complex A had an available iodine content of from about 27.5–29.5% by weight and a total iodine content of 37.0–41.0% by weight.

TABLE 2

| | 0.75% Available Iodine (Nominal) | |
|---|---|---|
| | 11 | 12 |
| Povidone K-30 | — | — |
| Nonoxynol 10 | — | — |
| Poloxamer 335 | 3 | 3 |
| Available Iodine | 0.75 | 0.75 |
| Iodide | 0.09 | 0.1 |
| Citric Acid | 0.1 | 0.1 |
| Glycerin | 0.5 | 0.5 |
| Sodium Iodate | 0.1 | 0.1 |
| Water | q.s. 100% | q.s. 100% |
| Initial pH | 4.1 | 4.5 |
| 3 Mos. pH | 4.4 | 4.6 |
| Initial Available $I_2$ | .70 | .70 |
| 3 Mos. Available $I_2$ | .71 | .70 |
| Initial Free $I_2$ (ppm) | 30 | 29 |
| 3 Mos. Free $I_2$ (ppm) | 42 | 29 |

TABLE 3

| | 0.50% Available Iodine | | | |
|---|---|---|---|---|
| | 13 | 14 | 15 | 16 |
| Poloxamer 403 | 1.25 | 1.25 | — | — |
| Povidone K-30 | — | — | 2.5 | 2.5 |
| Iodine Complex A | 1.50 | 1.50 | 1.50 | 1.50 |
| Citric Acid | 0.1 | 0.1 | 0.1 | 0.1 |
| Glycerin | 2.0 | 2.0 | 2.0 | 2.0 |
| Sodium Iodate | 0.2 | 0.2 | 0.2 | 0.2 |
| Water | q.s. 100% | q.s. 100% | q.s. 100% | q.s. 100% |
| Initial pH | 3.5 | 4.0 | 3.5 | 4.0 |
| 3 Mos. pH | 3.9 | 4.2 | 4.2 | 4.4 |
| Initial Available $I_2$ | .51 | .51 | .50 | .49 |
| 3 Mos. Available $I_2$ | .52 | .51 | .50 | .49 |
| Initial Free $I_2$ (ppm) | 31 | 22 | 27 | 19 |
| 3 Mos. Free $I_2$ (ppm) | 47 | 37 | 31 | 24 |

TABLE 4

| | 0.25% Available Iodine | | | |
|---|---|---|---|---|
| | 17 | 18 | 19 | 20 |
| Poloxamer 403 | 1.0 | 1.0 | 1.0 | 1.0 |
| Iodine Complex B[1] | 0.38 | 0.38 | 0.35 | 0.35 |
| Citric Acid | 0.1 | 0.1 | 0.1 | 0.1 |
| Viscosity Agent[2] | 0.05 | 0.05 | 0.05 | 0.05 |
| Glycerin | 2.0 | 2.0 | 2.0 | 2.0 |
| Sodium Iodate | 0.1 | 0.1 | 0.1 | 0.1 |
| Water | q.s. 100% | q.s. 100% | q.s. 100% | q.s. 100% |
| Initial pH | 3.6 | 3.3 | 4.0 | 3.6 |
| 3 Mos. pH | 3.6 | 3.4 | 4.1 | 3.5 |
| Initial Available $I_2$ | .25 | .22 | .24 | .22 |
| 3 Mos. Available $I_2$ | .26 | .24 | .25 | .24 |
| Initial Free $I_2$ (ppm) | 13 | 19 | 10 | 17 |
| 3 Mos. Free $I_2$ (ppm) | 21 | 16 | 24 | 23 |

[1]Iodine Complex B had an available iodine content of from about 56.0–58.0% by weight and a total iodine content of 75.0–79.0% by weight

[2]Xanthan gum

TABLE 5

0.10% Available Iodine

|  | 21 | 22 | 23 | 24 | 25 | 26 | 27 |
|---|---|---|---|---|---|---|---|
| Poloxamer 335 | — | — | — | — | 0.25 | 0.25 | — |
| Polysorbate 80 | — | — | — | — | 0.2 | 0.2 | — |
| Poloxamer 403 | — | — | — | — | — | — | 0.5 |
| Povidone K-30 | 0.25 | 0.50 | 1.0 | 1.0 | — | — | — |
| Iodine Complex A | 0.30 | 0.30 | 0.30 | 0.30 | 0.30 | 0.30 | 0.32 |
| Citric Acid | 0.05 | 0.05 | 0.05 | 0.05 | 0.05 | 0.05 | 0.05 |
| Glycerin | 0.15 | 0.15 | 0.15 | 0.15 | 2.05 | 2.0 | 2.0 |
| Sodium Iodate | 0.1 | 0.1 | 0.1 | 0.1 | 0.1 | 0.1 | 0.1 |
| Water | q.s. 100% | q.s. 100% | q.s. 100% | q.s. 100% | q.s. 100% | q.s. 100% | q.s. 100% |
| Initial pH | 3.0 | 3.0 | 3.0 | 2.7 | 3.8 | 3.7 | 3.0 |
| 3 Mos. pH | 3.6 | 3.6 | 3.6 | 2.8 | 4.6 | 4.4 | 3.3 |
| Initial Available $I_2$ | .09 | .09 | .09 | .09 | .09 | .08 | .10 |
| 3 Mos. Available $I_2$ | .10 | .10 | .10 | .12 | .11 | .10 | .11 |
| Initial Free $I_2$ (ppm) | 44 | 40 | 37 | 68 | 14 | 14 | — |
| 3 Mos. Free $I_2$ (ppm) | 52 | 46 | 42 | 78 | 17 | 16 | 53 |

TABLE 6

0.05% Available Iodine

|  | 28 | 29 | 30 | 31 | 32 |
|---|---|---|---|---|---|
| Nonoxynol 12 | 0.50 | 0.50 | 0.50 | — | — |
| Povidone K-30 | — | — | — | 0.10 | 0.20 |
| Iodine Complex A | 0.15 | 0.15 | 0.15 | 0.15 | 0.15 |
| Citric Acid | 0.05 | 0.05 | 0.05 | 0.05 | 0.05 |
| Sodium Iodate | 0.1 | 0.1 | 0.1 | 0.05 | 0.05 |
| Water | q.s. 100% | q.s. 100% | q.s. 100% | q.s. 100% | q.s. 100% |
| Initial pH | 3.0 | 2.7 | 2.4 | 2.2 | 2.2 |
| 3 Mos. pH | 3.1 | 2.9 | 2.7 | 2.3 | 2.3 |
| Initial Available $I_2$ | .05 | .05 | .05 | .04 | .04 |
| 3 Mos. Available $I_2$ | .04 | .05 | .03 | .06 | .05 |
| Initial Free $I_2$ (ppm) | 55 | 55 | 66 | 87 | 77 |
| 3 Mos. Free $I_2$ (ppm) | 49 | 45 | 45 | 116 | 115 |

TABLE 7

0.025% Available Iodine

|  | 33 | 34 |
|---|---|---|
| Povidone K-30 | 0.1 | 0.1 |
| Iodine Complex A | 0.075 | 0.075 |
| Citric Acid | .05 | .05 |
| Sodium Iodate | .05 | .10 |
| Water | q.s. 100% | q.s. 100% |
| Initial pH | 2.0 | 2.0 |
| 3 Mos. pH | 2.1 | 2.1 |
| Initial Available $I_2$ | .025 | .024 |
| 3 Mos. Available $I_2$ | .019 | .023 |
| Initial Free $I_2$ (ppm) | 114 | 104 |
| 3 Mos. Free $I_2$ (ppm) | 130 | 118 |

We claim:

1. A stable aqueous germicidal composition comprising:

from about 0.01–1.4% by weight available iodine;

from about 10–125 ppm free iodine;

from about 0.005–0.5% by weight iodate ion;

a quantity of complexing agent sufficient for maintaining said available iodine in solution;

from about 0.004–0.50% by weight iodide ion; and said composition having a pH of from about 2.0–4.5 and substantially maintaining the amounts of said available iodine and free iodine over a period of at least three months at room temperature storage.

2. The composition of claim 1, said composition having an available iodine level of from about 0.01–0.2% by weight.

3. The composition of claim 1, said composition having an available iodine level of from about 0.10–1.4% by weight.

4. The composition of claim 1, wherein said free iodine level is from about 25–125 ppm.

5. The composition of claim 1, wherein said iodate ion level is from about 0.01–0.4% by weight.

6. The composition of claim 1, wherein said complexing agent is present at a level of from about 0.1–15% by weight.

7. The composition of claim 1, said composition substantially maintaining said amounts of available iodine and free iodine for a period of at least about one year.

8. The composition of claim 1, including a buffering agent selected from the group consisting of citric acid, acetic acid, propionic acid, lactic acid, phosphoric acid, salts of the foregoing, and mixtures thereof.

9. The composition of claim 8, said buffering agent being present at a level of from about 0.02–1% by weight.

10. The composition of claim 1, said complexing agent being selected from the group consisting of the alkylphenol ethoxylates, alcohol ethoxylates, alcohol alkoxylates, polyalkylene glycol ethers, polyoxyethylene sorbitan monolaurate and monopalmitate, polyvinylpyrrolidone, polyethoxylated polyoxypropylenes, and mixtures thereof.

11. The composition of claim 1, including a thickening agent.

12. The composition of claim 11, said thickening agent being selected from the group consisting of alginates, xanthan gums, cellulose- bearing agents, and mixtures thereof.

13. The composition of claim 11, said thickening agent being present at a level of from about 0.05–1.5% by weight.

14. The composition of claim 1, including an emollient.

15. The composition of claim 14, said emollient being selected from the group consisting of glycerin, lanolin, sorbitol, fatty acid esters of polyhydroxylated compounds, propylene glycol, and mixtures thereof.

16. The composition of claim 14, said emollient being present at a level from about 1–15% by weight.

17. An aqueous germicidal composition which comprises respective amounts of available iodine, free iodine, iodate ion, iodide ion, and a complexing agent, said composition having at least about 25 ppm free iodine over a period of at least about 3 months at ambient temperature storage.

18. The use composition of claim 17, said composition having at least about 40 ppm free iodine over a period of at least 3 months at ambient temperature storage.

19. A stable aqueous germicidal composition comprising:

from about 0.01–1.4% by weight available iodine;

at least about 25 ppm free iodine;

from about 0.005–0.5% by weight iodate ion;

a quantity of complexing agent sufficient for maintaining said available iodine in solution;

from about 0.004–0.50% by weight iodide ion; and said composition having a pH of from about 2–5.5 and substantially maintaining the amounts of said available iodine and free iodine over a period of at least three months at room temperature storage.

20. The composition of claim 19, said composition having an available iodine level of from about 0.01–0.2% by weight.

21. The composition of claim 19, said composition having an available iodine level of from about 0.10–1.4% by weight.

22. The composition of claim 19, wherein said free iodine level is from about 25–125 ppm.

23. The composition of claim 19, wherein said iodate ion level is from about 0.01–0.4% by weight.

24. The composition of claim 19, wherein said complexing agent is present at a level of from about 0.1–15% by weight.

25. The composition of claim 19, wherein said pH is from about 2.0–4.5.

26. The composition of claim 19, said composition substantially maintaining said amounts of available iodine and free iodine for a period of at least about one year.

27. The composition of claim 19, including a buffering agent selected from the group consisting of citric acid, acetic acid, propionic acid, lactic acid, phosphoric acid, salts of the foregoing, and mixtures thereof.

28. The composition of claim 27, said buffering agent being present at a level of from about 0.02–1% by weight.

29. The composition of claim 19, said complexing agent being selected from the group consisting of the alkylphenol ethoxylates, alcohol ethoxylates, alcohol alkoxylates, polyalkylene glycol ethers, polyoxyethylene sorbitan monolaurate and monopalmitate, polyvinylpyrrolidone, polyethoxylated polyoxypropylenes, and mixtures thereof.

30. The composition of claim 19, including a thickening agent.

31. The composition of claim 30, said thickening agent being selected from the group consisting of alginates, xanthan gums, cellulose-bearing agents, and mixtures thereof.

32. The composition of claim 30, said thickening agent being present at a level of from about 0.05–1.5% by weight.

33. The composition of claim 19, including an emollient.

34. The composition of claim 33, said emollient being selected from the group consisting of glycerin, lanolin, sorbitol, fatty acid esters of polyhydroxylated compounds, propylene glycol, and mixtures thereof.

35. The composition of claim 34, said emollient being present at a level from about 1–15% by weight.

* * * * *